United States Patent [19]
Rasmussen

[11] Patent Number: 5,925,282
[45] Date of Patent: Jul. 20, 1999

[54] METHOD OF MANUFACTURING A FOIL-WRAPPED BREAST PROSTHESIS AND A SHAPING TOOL FOR USE IN PERFORMING THE METHOD

[75] Inventor: Laurits Boye Rasmussen, Smidstrup, Denmark

[73] Assignee: Coloplast A/S, Denmark

[21] Appl. No.: 08/663,298

[22] PCT Filed: Dec. 21, 1994

[86] PCT No.: PCT/DK94/00479

§ 371 Date: Jun. 21, 1996

§ 102(e) Date: Jun. 21, 1996

[87] PCT Pub. No.: WO95/17141

PCT Pub. Date: Jun. 29, 1995

[30] Foreign Application Priority Data

Dec. 23, 1993 [DK] Denmark .................................. 1444/93

[51] Int. Cl.⁶ .............................. A61F 2/62; B29K 51/10
[52] U.S. Cl. ........................... 249/55; 249/170; 249/171; 425/521
[58] Field of Search ..................................... 156/242, 245, 156/290, 308.4, 221, 292; 264/259, 266, 222, 511, 571, DIG. 78, DIG. 30, 239, 46.6; 623/7, 8, 401; 425/521, 423, DIG. 60; 249/55, 170, 171, 142

[56] References Cited

U.S. PATENT DOCUMENTS 4,247,351  1/1981  Rechenberg .
4,249,975  2/1981  Rechenberg ................................ 56/245
4,401,492  8/1983  Pfrommer .................................. 264/222
4,701,230  10/1987 Loi .

FOREIGN PATENT DOCUMENTS 0429029  5/1991  European Pat. Off. .
2564728  11/1985 France .
2604744  8/1977  Germany .
3336279  1/1986  Germany .
2257387  1/1993  United Kingdom .

*Primary Examiner*—Richard Crispino
*Attorney, Agent, or Firm*—Ostrolenk, Faber, Gerb & Soffen, LLP

[57] ABSTRACT

When manufacturing a foil-wrapped breast prosthesis with a filling consisting of a curable compound, the curing is performed after placing a filled prosthesis bag formed by two joined foil sheets in a mold cavity without closing the mold cavity and maintaining vacuum at least in the beginning of the curing, whereby especially an increased degree of freedom is obtained with respect to shaping the rear side of the prosthesis, so that this, among other things, can be provided with thin edge parts for obtaining good fitting to the body. To ease the mounting of the bag and the accurate positioning of this in the mold cavity, the latter is formed in a first mold part of a shaping tool, which furthermore comprises a tightening frame having a packing, which provides an unambiguously oriented tightening of the bag when this is placed in the mold cavity.

9 Claims, 5 Drawing Sheets

METHOD OF MANUFACTURING A FOIL-WRAPPED BREAST PROSTHESIS AND A SHAPING TOOL FOR USE IN PERFORMING THE METHOD

The invention relates to a method of manufacturing a foil-wrapped breast prosthesis with a filling consisting of a curable compound, preferably a silicone compound, by which at least two foil sheets of a formable plastic material are joined for producing a prosthesis bag, leaving at the joint a filling opening, through which the bag is filled with a quantity of said compound and the filling opening is sealed after air bubbles have been expelled, the filled prosthesis bag is placed in a mould having a first mould part with an open mould cavity corresponding to the desired shape of the front of the prosthesis, the bag being positioned with respect to the mould cavity and secured to the mould, whereafter the filling is cured and the moulded prosthesis is removed from the mould.

The invention also relates to a shaping tool for use in performing the method.

From DE-C2-33 36 279 and U.S. Pat. No. 4,249,975 methods of manufacturing breast prostheses are known by which injection of the silicone compound used as filling is performed under pressure during the actual curing process, which is performed in a closed mould. In this connection, it is known from said DE publication to bring the walls of the prosthesis bag into contact with the walls of the mould cavity by applying vacuum before injecting the silicone compound.

To avoid the disadvantages by injecting the silicone compound under pressure during the actual curing process, a manufacturing method of the above mentioned kind is suggested in GB-A-2 257 387, by which the prosthesis bag is filled before being placed in the curing mould, which also in this case is closed, the actual mounting taking place under application of vacuum.

In a method of the above mentioned kind, the manufacturing can be performed in practice e.g. by welding together two sheets of polyurethane foil, which have been pre-shaped for forming the front and the rear side, respectively, of the prosthesis, into a prosthesis bag by means of a contour welding tool, thereby leaving a gate for use in filling the curable prosthesis mass, which usually consists of a vulcanizable silicone compound. By the filling, a predetermined volume of the filling compound is admitted to the prosthesis bag by means of conventional mixing and dosing equipment, whereafter the gate is sealed by high-frequency or hot welding, possibly after having expelled air bubbles.

However, for the method according to the above mentioned GB patent application, an over-charging of the prosthesis bag is required to obtain a fully moulded front with an intended anatomic shape with a nipple, which generally results in an unintentional thickening of the prosthesis edge, the prosthesis thus not fitting tightly to the body.

The purpose of the invention is to provide a method by which the above mentioned problem can be avoided, and a shaping tool which to a considerable extent eases the handling of a prosthesis bag by placing and fixing it in a mould or a curing shell.

In this respect, according to the invention a method of the above mentioned kind is characterized in that the curing is performed without closing the mould cavity and while maintaining vacuum therein, at least in the beginning of the curing.

As the front of the prosthesis bag is kept in close contact with the wall of the mould cavity until the filling, or at least the part of it which is close to the wall, has cured, a considerably improved certainty is obtained for a fully moulded front with the desired shape corresponding to the mould cavity in the generally replaceable first mould part and with thin edge parts, making the prosthesis fit well to the body.

At the same time, greater freedom in the elaboration of the rear side of the prosthesis is obtained, as an expansion of the prosthesis mass, as a result of thermal expansion during the curing, can be routed to the areas of the rear side which are less important to the appearance and function of the prosthesis.

As such method according to the invention can be performed without using a rear block, although such a rear block is applied in most cases to obtain a desired shaping of parts of the rear side of the prosthesis. The shaping of the rear side can also be utilized for adjusting the flexibility and elasticity of the prosthesis and, in case of large prostheses, possibly for adjusting the weight of the prosthesis.

The maintaining of vacuum during the curing must be of such duration that at least the part of the filling which is close to the front wall of the prosthesis has cured sufficiently. The duration of this period will depend and partly on the size of the prosthesis, partly on the curing temperature. For practical reasons, it will often be preferable to maintain vacuum during the whole curing process.

The application of vacuum, at least in the beginning of the curing process, makes it unnecessary to dose the bag accurately to obtain well-defined front and rear sides, as the front is retained while at the same time the critical parts of the rear side can be shaped as desired. Thereby inter alia, sub-filling of the bag, due to a too small dosing or unfavourable thermal/curing conditions, can be shifted to less critical areas of the rear side.

In this way, better control of the quality of the finished product is obtained.

In addition, the rear side of the prosthesis can be elaborated with thin edges for obtaining form-fit contact with the body.

As by the method according to the invention shaping is preferably performed of the foil wall intended to form the rear side of the prosthesis, by bringing a rear block into contact with the prosthesis bag placed in the mould cavity without closing the cavity, such a rear block can, for manufacturing self-supported breast prostheses, be utilized with advantage for placing stitching elements, which are subsequently transferred to the prosthesis bag by welding during the curing.

The shaping tool according to the invention provided for use in performing the method is of the type which comprises a first mould part having an open mould cavity corresponding to the desired shape of the front of a breast prosthesis, means for providing vacuum in said mould cavity, and means for tightening the parts of the joined foil sheets in a prosthesis bag which are placed outside the joint placed at the opening edge of the mould cavity.

For obtaining simple handling of a prosthesis bag in connection with mounting and fixing, the shaping tool is characterized in that said tightening means comprise a tightening frame connected with the first mould part, which frame has a packing for abutment with the parts of the foil sheets which are situated outside the opening edge of the first mould part at the placing of the prosthesis bag in the first mould part, and that at least one rear block is connected with the tightening frame in such a way as to allow said shaping of the rear wall of a prosthesis bag placed in the first mould part to be performed without closing the mould cavity. In a preferred embodiment, the packing is designed in such a way that, after closing the frame with respect to the first mould part, it permits tightening of said foil sheets by stretching in only one direction in the packing plane away from the mould cavity, but prevents movement of the foil sheets in the other direction, whereby the joint is made to be flush with the opening edge of the mould cavity. Hereby the otherwise rather complicated tightening process is facilitated and accurate positioning of the prosthesis bag in the mould cavity is secured.

BRIEF DESCRIPTION OF THE DRAWINGS

In the following the invention will be described in detail with reference to the drawing, in which.

DESCRIPTION OF THE DRAWINGS

Figure 1:
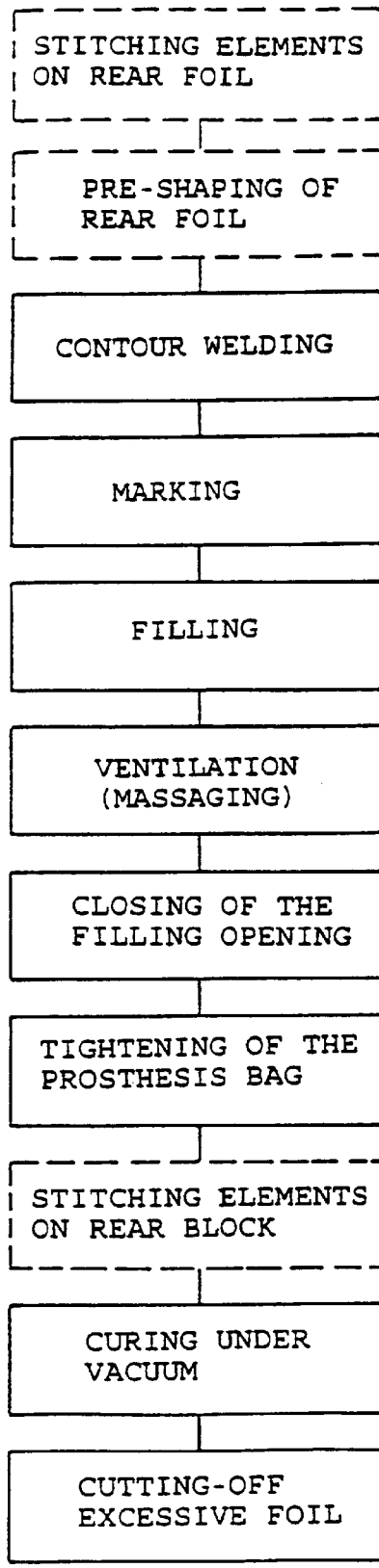
FIG. 1 is a flow diagram illustrating the main steps in the manufacturing of breast prostheses by the method according to the invention.
Figure 2:
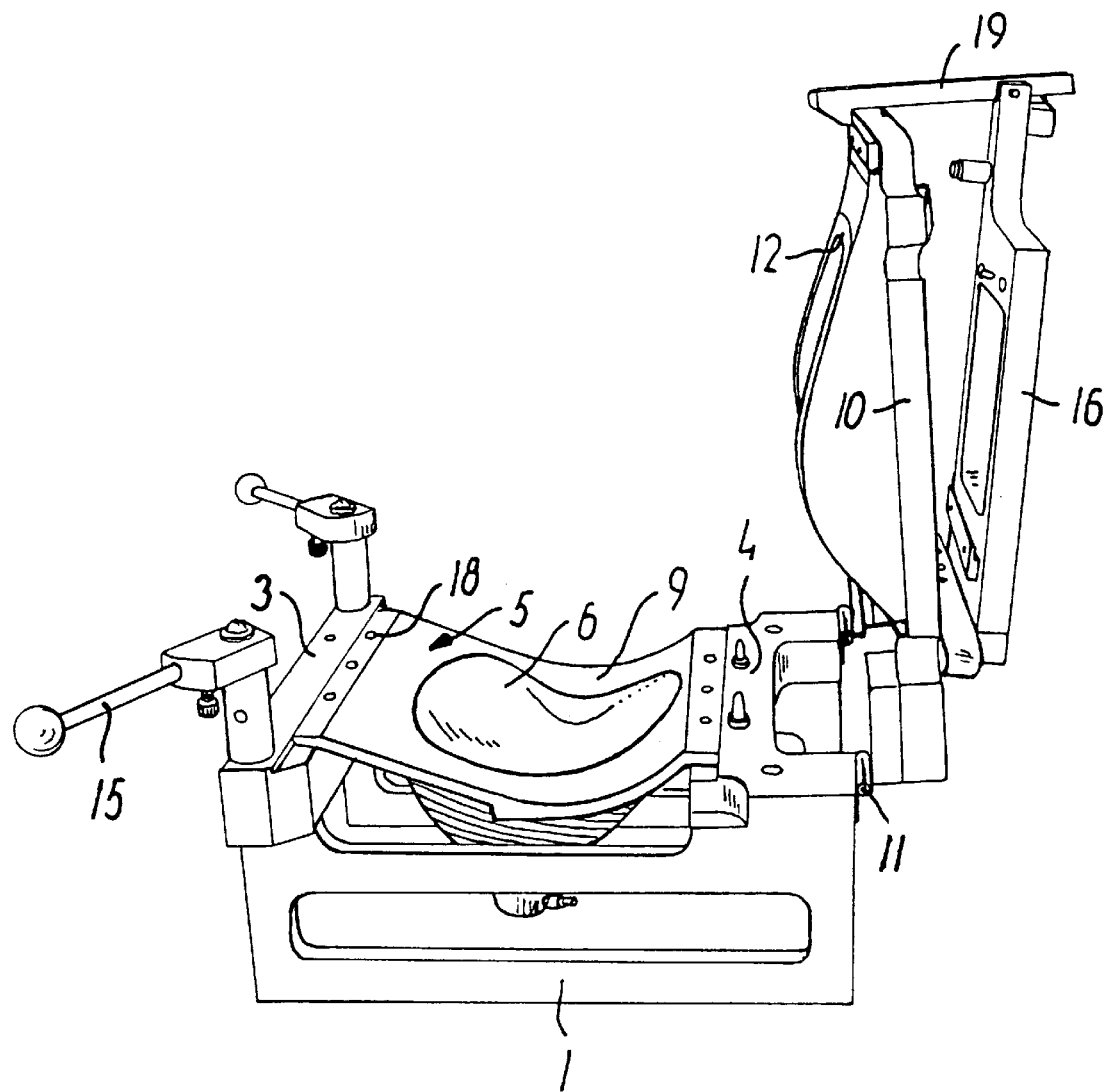
FIGS. 2–4 are perspective views of an embodiment of a shaping tool according to the invention in three different positions.

The flow diagram in FIG. 1 is a schematic illustration of the manufacturing of a self-supported breast prosthesis, the rear side of which must be provided with stitching elements, e.g. velcro elements for adhesive attachment to the skin of the user, in order to secure the prosthesis to the body.

In the embodiment shown, the manufacturing can, in a manner known per se, start by placing such velcro elements on the one of the two foil sheets which is intended to form the rear side of the finished prosthesis.

In the cases where it is required by the shaping of the prosthesis, preforming by thermoforming can subsequently be performed of the rear foil, which, like the front foil, may typically be a polyurethane foil.

However, these two initial steps are not necessary, as in many cases preforming of the rear side can be omitted and the invention offers the possibility of using a rear block, which is used for shaping the rear side of the prosthesis during the curing, for placing the velcro elements, which are subsequently transferred to the prosthesis bag by welding during the curing, thereby saving one production step.

The two foil sheets are welded together, possibly after having performed the two above mentioned initial steps, into a prosthesis bag by means of a contour welding tool of a kind known per se, this welding leaving a filling opening for filling the prosthesis mass, which preferably consists of a vulcanizable silicone compound with various additives, e.g. dye.

It is hereby noted that by the method according to the invention, no preforming of the front foil is performed.

When the prosthesis bag has been marked, e.g. with type identifying mark and number, the silicone compound is filled into the bag by means of standard mixing and dosing equipment. It is hereby noted that by the method according to the invention, the filled quantity of the compound is less critical than with known manufacturing methods, as a result of the increased degree of freedom with respect to shaping the rear side of the prosthesis.

After some time, possible small air bubbles in the filled compound, which has a gel-like consistency, are expelled through the filling opening, e.g. by massaging the bag or by means of vacuum, as it is known from the above mentioned GB patent application, and the filling opening is then sealed by high-frequency or hot welding.

For production reasons, it may be advantageous to store the prosthesis bags thus filled and sealed, which can be done by cold storage, as it is also explained in the above mentioned GB-A-2 257 387.

Finishing of the breast prosthesis is then done by placing a filled and sealed bag, which can be elaborated with or without a preformed rear side and with or without stitching elements in the form of velcro elements, in a shaping tool and fixing it therein, which shaping tool can be designed as explained in further detail in the following.

At the fixing, the contour weld of the bag is made to be flush with the opening edge of a mould cavity in a lower part of the shaping tool by tightening the foil sheets, which mould cavity corresponds to the desired shape of the breast prosthesis, and hereby the front foil of the bag can be brought into close contact with the wall of the mould cavity by applying vacuum to the mould cavity.

As explained in the following, a shaping tool having an open cavity is used for the method according to the invention during the subsequent curing process, during which vacuum is applied or applied vacuum is maintained at least long enough to cure the part of the silicone compound in the bag which is the closest to the front wall of the bag.

Optionally, the mold cavity may include a hollow in the shape of a nipple, whereby a corresponding nipple will be formed on the front side of the prothesis when the filling compound is cured.

The open mould cavity results in a considerable degree of freedom with respect to post-shaping of the rear wall of the prosthesis, which can be done by means of a rear block forming part of the shaping tool.

The curing process, by which the silicone compound is vulcanized, is performed in a manner known per se in a curing oven at a temperature and for a period of time which depend on the silicone compound applied.

After the curing, the prosthesis is removed from the shaping tool and the parts of the joined foil sheets situated outside the contour weld are cut off, after which the prosthesis can be finished by washing, sorting and packing.

In the embodiment shown in FIGS. 2–5, the shaping tool comprises a base frame with upright side parts 1 and 2, which at the front and at the back are connected with cross parts 3 and 4.

The base frame 1–4 is designed for detachable mounting of a first mould part 5, in which a hollow 6 forms an upwards open mould cavity with a wall shape corresponding to the desired front shape of the present breast prosthesis.

Figure 5:
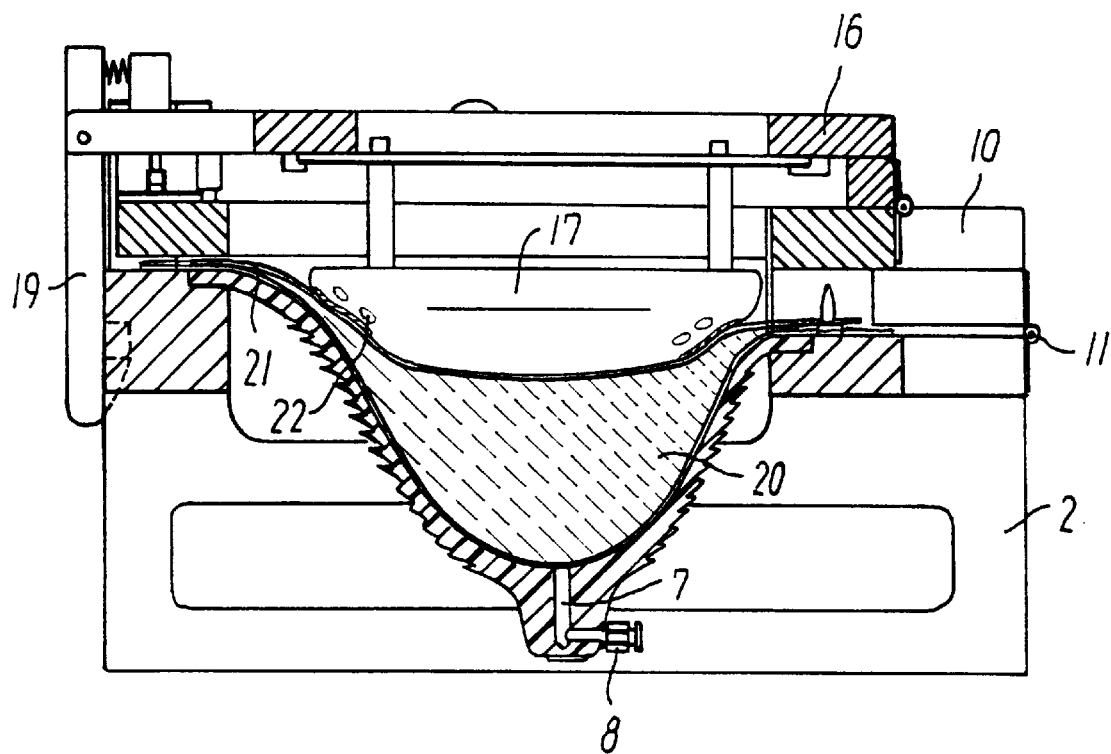
FIG. 5 is a sectional view of the shaping tool shown in FIGS. 2–4.

As it will appear most clearly from FIG. 5, an air duct 7 having a valve 8 is connected at the bottom of the mould cavity 6, which air duct is to be used when applying vacuum to the mould cavity through a non-illustrated hose coupling.

With a view to accurate positioning in the base frame, the mould part 5 is provided with a number of positioning holes 18 for arrangement on guide pins on the top side of the base frame.

The top side of the mould part 5 is formed by a downwards curved top plate 9 having a shape determined by the desired contour of the rear edge of the prosthesis, so that a good fitting to the body of the rear side of the prosthesis can be obtained.

In the embodiment shown, a tightening frame 10 is pivotally connected with the top edge of the rear part 4 of the base frame by means of hinges 11.

Figure 3:
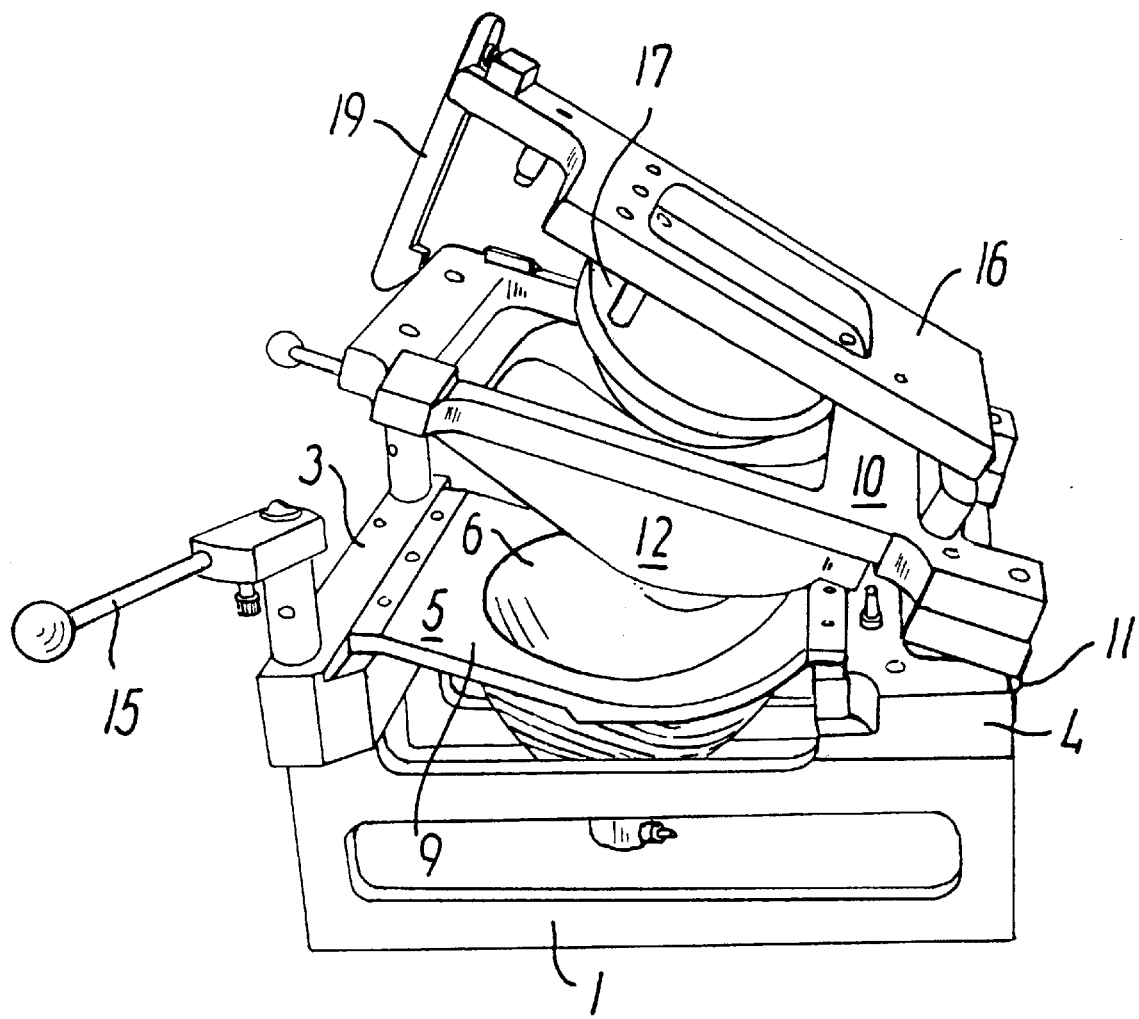

As it can be seen most clearly in FIG. 3, the tightening frame 10 is designed as a principally rectangular frame, to the underside of which is attached a packing 12 of an elastic, semirigid packing material, e.g. silicone. The packing 12 is attached to the tightening frame 10 in such a way that it curves outwards in the direction away from the frame by a curvature corresponding to the curved top plate of the mould part 5.

Figure 4:
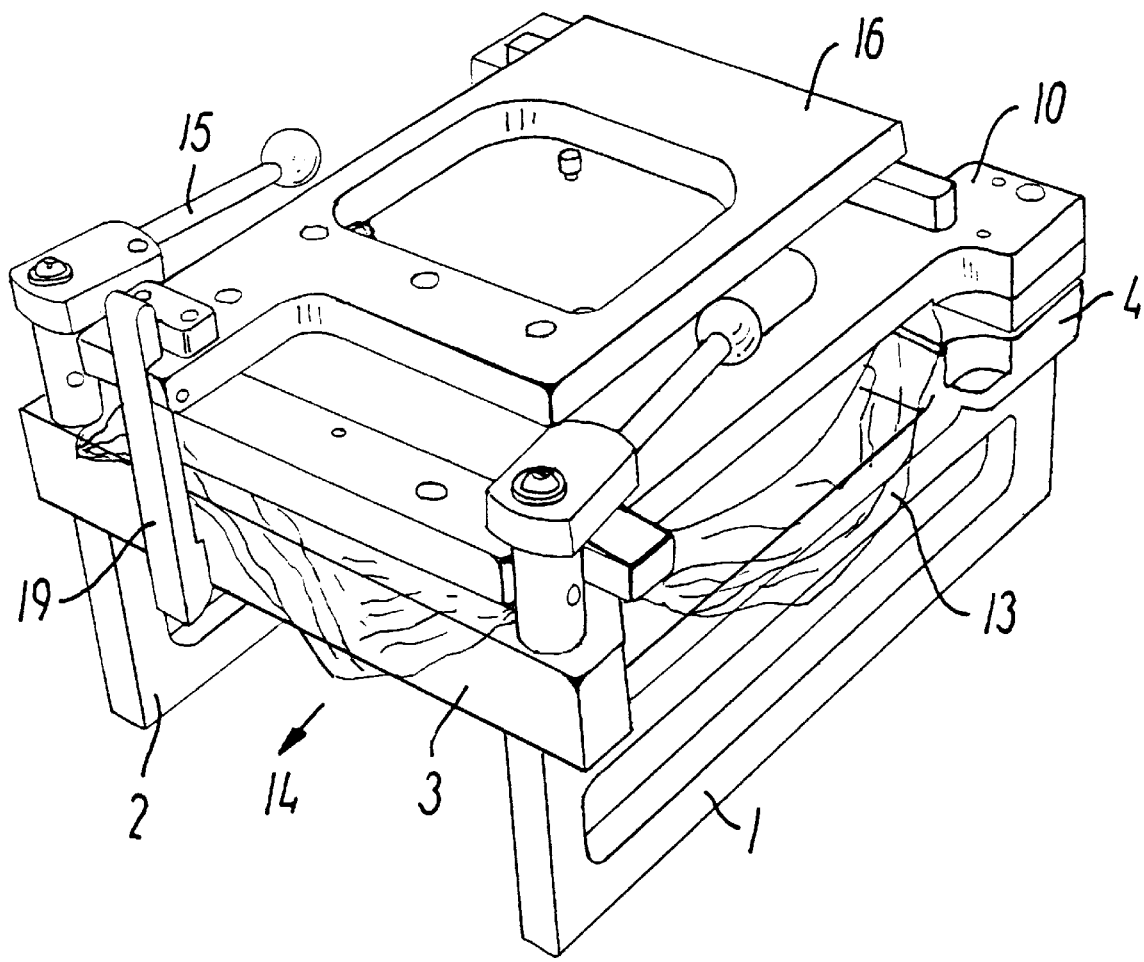

The illustrated design of the packing 12 and the hinge connection of the tightening frame 10 with the rear part 4 of the base frame implies that the packing 12, when closing the tightening frame 10 on a filled prosthesis bag placed in the mould cavity 6, will be brought into contact with the parts of the joined foil sheets shown at 13 in FIG. 4 which are placed immediately outside the contour weld, in such a way that tightening of the foil sheets can only be done by stretching the sheets in only one direction in the packing plane, i.e. perpendicular to the pivot axis which is determined by the hinges 11 and in the direction away from this axis, as shown by the arrow 14 in FIG. 4, while the packing prevents movement of the foil sheets in other directions. Hereby a very accurate and reproducible positioning of the prosthesis bag in the mould cavity 6 is obtained.

After closing the tightening frame 10, this is fixed at the front part 3 of the base frame by means of locking handles 15.

In addition, a principally rectangular top frame 16 is pivotally connected with the tightening frame 10, on the underside of which top frame a rear block 17 can be detachably mounted, by which the rear wall of the prosthesis 20 can be given a desired shape during the curing, e.g. with the object of obtaining thin edge zones 21 within the contour weld of the prosthesis for providing optimum body fitting of a self-supported prosthesis.

As it will appear from FIGS. 4 and 5, closing of the top frame 16, whether or not this is provided with a rear block, will not cause any closing of the mould cavity 6, but this is kept upwards open during the whole shaping process including the curing. At the closing, the top frame 16 is clamped to the front part 1 of the base frame by means of a spring-loaded latch 19.

As explained in the above and illustrated in FIG. 5, the rear block 17 may be provided with recesses 22 or the like for receiving velcro pieces in connection with production of self-supported prostheses, such velcro parts thus being transferred to the rear side of the prosthesis by welding during the curing.

Figure 6:
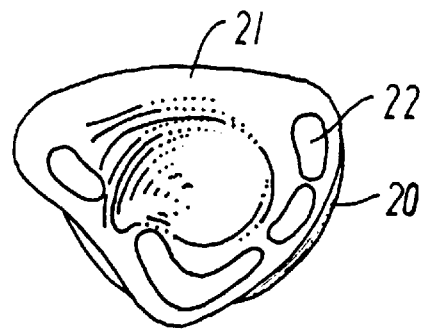
FIG. 6 is a rear view a the finished breast prosthesis.

FIG. 6 shows a typical example of the design of the rear side of a breast prosthesis 20 manufactured by means of the method and the shaping tool according to the invention and with velcro parts 22 attached for providing safe attachment to the skin.

I claim:

1. An apparatus for manufacturing a moulded foil-wrapped breast prosthesis comprising a mould having a first mould part with an open mould cavity having a surface corresponding to a desired shape of a front side of a breast prosthesis and arranged to receive a preformed prosthesis bag comprising two foil sheets joined by a sealed contour joint and filled with a quantity of a curable compound with said contour joint located against an opening edge of said mould cavity, said apparatus further comprising means for applying vacuum to said mould cavity and means for tightening parts of the joined foil sheets situated outside said opening edge of the mould cavity, characterized in that said tightening means comprises a tightening frame pivotally connected with said first mould part and having a packing for engaging said parts of the foil sheets situated outside said opening edge of the mould cavity when said tightening frame is pivotally moved to a closing position with respect to said first mould part, and a rear block pivotally connected with said tightening frame for shaping a rear side of said prosthesis bag when placed in said first mould part without closing the mould.

2. An apparatus according to claim 1, characterized in that said packing is adapted to tighten said parts of the foil sheets by stretching in one direction only away from the mould cavity in a packing plane defined by said closing position of the tightening frame, and preventing movement of the foil sheets in other directions in said packing plane, whereby said contour joint is positioned to be flush with the opening edge of the mould cavity.

3. An apparatus according to claim 1, characterized in that said rear block is pivotally connected with the tightening frame for shaping said rear side of the prosthesis bag subsequent to the tightening of said foil sheets by the tightening frame.

4. An apparatus according to claim 1, characterized in that said rear block is detachably mounted on an underside of a top frame pivotally connected with said tightening frame.

5. An apparatus according to claim 1, characterized in that the parts of the first mould part and the tightening frame intended for engagement with a prosthesis bag are black-oxidized or black-anodized metal parts.

6. An apparatus as claimed in claim 1, characterized in that said rear block has recesses for receiving stitching elements to be transferred to said rear side of a prosthesis bag during the curing process.

7. An apparatus according to claim 6, characterized in that said rear block is detachably mounted on an underside of a top frame pivotally connected with said tightening frame and said rear block is pivotally connected with the tightening frame for shaping said rear side of the prosthesis bag subsequent to the tightening of said foil sheets by the tightening frame.

8. An apparatus according to claim 7, characterized in that said rear block is pivotally connected with the tightening frame for shaping said rear side of the prosthesis bag subsequent to the tightening of said foil sheets by the tightening frame.

9. An apparatus according to claim 8, characterized in that said packing is adapted to tighten said parts of the foil sheets by stretching in one direction only away from the mould cavity in a packing plane defined by said closing position of the tightening frame, and preventing movement of the foil sheets in other directions in said packing plane, whereby said contour joint is positioned to be flush with the opening edge of the mould cavity.

* * * * *